United States Patent [19]
Harpold et al.

[11] Patent Number: 5,401,629
[45] Date of Patent: Mar. 28, 1995

[54] ASSAY METHODS AND COMPOSITIONS USEFUL FOR MEASURING THE TRANSDUCTION OF AN INTRACELLULAR SIGNAL

[75] Inventors: Michael M. Harpold; Paul Brust, both of San Diego, Calif.

[73] Assignee: The Salk Institute Biotechnology/Industrial Associates, Inc., San Diego, Calif.

[21] Appl. No.: 563,751

[22] Filed: Aug. 7, 1990

[51] Int. Cl.⁶ ............................................. C12Q 1/68
[52] U.S. Cl. ................................... 435/6; 435/172.3; 435/240.1; 436/63; 935/36; 935/39; 935/41
[58] Field of Search ................... 435/6, 172.3, 240.1; 436/63, 94; 935/36, 39, 41

[56] References Cited
U.S. PATENT DOCUMENTS

| | | | |
|---|---|---|---|
| 4,859,609 | 8/1989 | Dull et al. ........................ | 436/501 |
| 4,981,784 | 1/1991 | Evans et al. ..................... | 435/6 |
| 5,071,773 | 12/1991 | Evans et al. ..................... | 436/501 |
| 5,091,518 | 2/1992 | Sucov et al. ..................... | 536/27 |

OTHER PUBLICATIONS

Collins et al., Proc. Natl. Acad. Sci. USA, vol. 86., (Jul. 1989), pp. 4853–4857.
Allard, et al., "Sequence of the gene encoding the human M1 muscarinic acetylcholine receptor," *Nucl. Acids. Res.*, 15:10604 (1987).
Subramani, et al., "Expression of the mouse dihydrofolate complementary deoxyribonucleic reductase acid in simian virus 40," *Mol. Cell. Biol.*, 1:854–864 (1981).
Deschamps, et al., "Identification of a transcriptional enhancer element upstream from the proto-oncogen fos," *Science*, 230:1174–1177 (1985).
Michel, et al., "PC12 phaeochromocytoma cells contain an atypical muscarinic receptor binding site," *Br. J. Pharmacol.*, 97:914–920 (1989).
Lambert, et al., "Muscarinic receptor binding characteristics of a human neuroblastomas SK-N-SH and its clones SH-SY5Y and SH-EP1," *Eur. J. Pharmacol.*, 165:71–77 (1988).
Serra, et al., "The intact human neuroblastoma cell (SH-SY5Y) exhibits high-affinity [³H]pirenzepine binding associated with hydrolysis of phosphatidylinositols," *J. Neurochem.*, 50:1513–1521 (1988).
Serra, et al., "Phorbol esters alter muscarinic receptor binding and inhibit polyphosphoninositide breakdown in human neuroblastoma (SH-SY5Y) cells," *Biochem. Biophys. Res. Comm.*, 140:160–166 (1988).
Peralta, et al., "Differential regulation of PI hydrolysis and adenylyl cyclase by mascarinic receptor subtypes," *Nature*, 334:434–437 (1988).
Horowitz, et al., "Muscarinic receptor stimulation increases inositol-phospholipid metabolism and inhibits cyclic AMP accumulation in PC12 cells," *J. Neurochem.*, 53:197–204 (1989).
Bonner, et al., "Cloning and expression of the human and rat m5 muscarinic acetylcholine receptor genes," *Neuron*, 1:403–410 (1988).
Wada, et al., "Functional expression of a new pharmacological subtype of brain nicotinic acetylcholine receptor," *Science*, 240:330–334 (1988).
Boulter, et al., "Isolation of a cDNA clone coding for a possible neural nicotinic acetylcholine receptor α-subunit," *Nature*, 319:368–374 (1986).
Goldman, et al., "Members of a nicotinic acetylcholine receptor gene family are expressed in different regions of the mammalian central nervous system," *Cell*, 48:965–973 (1987).
Boulter, et al., "α3, α5, and β4: Three members of the rat neuronal nicotinic acetylcholine receptor-related gene family form a gene cluster," *J. Biol. Chem.*, 265:4472–4482 (1990).

(List continued on next page.)

*Primary Examiner*—Amelia Burgess Yarbrough
*Attorney, Agent, or Firm*—Brown, Martin, Haller & McClain

[57] ABSTRACT

Recombinant cells are provided which are useful for assaying compounds for their agonist or antagonist activity with respect to ion channels and/or cell surface-localized receptors. In addition, assay methods employing the invention recombinant cells are provided.

14 Claims, No Drawings

OTHER PUBLICATIONS

Deneris, et al., "Primary structure and expression of β2: A novel subunit of neuronal nicotinic acetylcholine receptors," *Neuron*, 1:45–54 (1988).

Deneris, et al., "β3: A new member of nicotinic acetylcholine receptor gene family is expressed in brain," *J. Biol. Chem.*, 264:6268–6272 (1989).

Duvoisin, et al., "The functional diversity of the neuronal nicotinic acetylcholine receptors is increased by a novel subunit: β4," *Neuron*, 3:487–496 (1989).

Schofield, et al., "Sequence and functional expression of the $GABA_A$ receptor shows a ligand-gated receptor super-family," *Nature*, 328:221–227 (1987).

Levitan, et al., "Structural and functional basis for $GABA_A$ receptor heterogeneity," *Nature*, 335:76–79 (1988).

Pritchett, et al., "Importance of a novel $GABA_A$ receptor subunit for benzodiazepine pharmacology," *Nature*, 338:582–585 (1989).

Ymer, et al., "$GABA_A$ receptor β subunit heterogeneity: functional expression of cloned cDNAs," *EMBO J.*, 8:1665–1670 (1989).

Shivers, B. D., "Two novel $GABA_A$ receptor subunits exist in distinct neuronal subpopulations," *Neuron*, 3:327–337 (1989).

Hollmann, et al., "Cloning by functional expression of a member of the glutamate receptor family," *Nature*, 342:643–648 (1989).

Frielle, et al., "Cloning of the cDNA for the human $β_1$-adrenergic receptor," *PNAS*, 84:7920–7924 (1987).

Kobilka, et al., "Cloning, sequencing, and expression of the gene coding for the human platelet $α_2$-adrenergic receptor," *Science*, 238:650–656 (1987).

Dixon, et al., "Cloning of the gene and cDNA for mammalian β-adrenergic receptor and homology with rhodopsin," *Nature*, 321:75–79 (1986).

Stormann, et al., "Molecular cloning and expression of a dopamine D2 receptor from human retina," *Molec. Pharm.* 37:1–6 (1990).

Bunzow, et al., "Cloning and expression of a rat $D_2$ dopamine receptor cDNA," *Nature*, 336:783–787 (1988).

Johnson, et al., "Expression and structure of the human NGF receptor," *Cell*, 47:545–554 (1986).

Kobilka, et al., "An intronless gene encoding a potential member of the fmaily of receptors coupled to guanine nucleotide regulatory proteins," *Nature*, 329:75–79 (1987).

Julius, et al., "The 5HT2 receptor defines a family of structurally distnict but functionally conserved serotonin receptors," *PNAS*, 87:928–932 (1990).

Julius, et al., "Molecular characterization of a functional cDNA encoding the serotonin 1c receptor," *Science*, 241:558–564 (1988).

Tanabe, et al., "Primary structure of the receptor for calcium channel b lockers from skeletal muscle," *Nature*, 328:313–318 (1987).

Ellis, et al., "Sequence and expression of mRNAS encoding the $α_1$ and $α_2$ subunits of a DHP-sensitive calcium channel," *Science*, 241:1661–1664 (1988).

Ruth, et al., "Primary structure of the β subunit of the DHP-sensitive calcium channel from skeletal muscle," *Science*, 245:1115–1118 (1989).

Jay, et al., "Primary structure of the γ subunit of the DHP-sensitive calcium channel from skeletal muscle," *Science*, 248:490–492 (1990).

McKinnon, D., "Isolation of a cDNA clone coding for a putative second potassium channel indicates the existence of a gene family," *J. Biol. Chem.*, 264:8230–8236 (1989).

Tempel, et al., "Cloning of a probable potassium channel gene from mouse brain," *Nature*, 332:837–839 (1988).

Noda, et al., "Existence of distinct sodium channel messenger RNAs in rat brain," *Nature*, 320:188–192 (1986).

Kayano, et al., "Primary structure of rat brain sodium channel III deduced from the cDNA sequence," *FEBS Lett.*, 228:187–194 (1988).

Fink, et al., "The CGTCA sequence motif is essential for biological activity of the vasoactive intestinal peptide gene cAMP-regulated enhancer," *Proc. Natl. Acad. Sci.*, 85:6662–6666 (1988).

Montminy, et al., "Identification of a cyclic-AMP-responsive element within the rat somatostatin gene," *Proc. Natl. Acad. Sci.*, 83:6682–6686 (1986).

Comb, et al., "A cyclic AMP- and phorbol ester-inducible DNA element," *Nature*, 323:353–356 (1986).

Short, et al., "Characterization of the phosphoenolpyruvate carboxykinase (GTP) promoter-regulatory region," *J. Biol. Chem.*, 261:9721–9726 (1986).

(List continued on next page.)

OTHER PUBLICATIONS

Changelian, et al., "Structure of the NGFI-A gene and detection of upstream sequences responsible for its transcriptional induction by nerve growth factor," *Proc. Natl. Acad. Sci.*, 86:377–381 (1989).

Visvader, et al., "Two adjacent promoter elements mediate nerve growth factor activation of the c-fos gene and bind distinct nuclear complexes," *PNAS*, 85:9474–9478 (1988).

Verma, et al., "Proto-Oncogene fos: Complex but versatile regulation," *Cell*, 51:513–514 (1987).

Sheng, et al., "The regulation and function of c-fos and other immediate early genes in the nervous system," *Neuron*, 4:477–485 (1990).

Lamb, et al., "Demonstration in living cells of an intragenic negative regulatory element within the rodent c-fos gene," *Cell*, 61:485–496 (1990).

Alton and Vapnek, "Nucleotide sequence analysis of the chloramphenicol resistance transposon tn9," *Nature*, 282:864–869 (1979).

deWet, et al., "Firefly luciferase gene: structure and expression in mammalian cells," *Mol. Cell. Biol.* 7:725–737 (1987).

Engebrecht and Silverman, "Identification of genes and gene products necessary for bacterial bioluminescence," *PNAS*, 1:4154–4158 (1984).

Baldwin, et al., "Cloning of the luciferase structural genes from vibrio harveyi and expression of bioluminescence in escherichia coli," *Biochemistry*, 23:3663–3667 (1984).

Toh, et al., "Isolation and characterization of a rat liver alkaline phosphatase gene," *Eur. J. Biochem.*, 182:231–238 (1989).

ASSAY METHODS AND COMPOSITIONS USEFUL FOR MEASURING THE TRANSDUCTION OF AN INTRACELLULAR SIGNAL

FIELD OF THE INVENTION

The present invention relates to methods and compositions useful for assaying the transduction of an intracellular signal in cells expressing cell surface-localized receptors and/or ion channels. In a particular aspect, the present invention relates to methods for assaying the agonist or antagonist activity of compounds with respect to cell surface-localized receptors and/or ion channels.

BACKGROUND OF THE INVENTION

Ion channels are membrane spanning proteins that allow controlled entry of various ions into cells from the extracellular fluid. All cells throughout the animal kingdom, as well as most bacterial, fungal, and plant cells, possess one or more types of ion channel. Similarly, cell surface-localized receptors control entry of various chemical species into cells from the extracellular fluid. As with ion channels, cell surface-localized receptors are found in nearly all members of the plant and animal kingdoms. Ion channels and cell surface-localized receptors are physiologically important, playing a central role in regulating intracellular levels of various ions and chemicals, many of which are important for cell viability and function.

A number of compounds useful in treating various diseases in animals, including humans, are thought to exert their beneficial effects by modulating the functioning of ion channels and/or cell surface-localized receptors.

An understanding of the pharmacology of compounds that interact with ion channels and/or cell-surface localized receptors, and the ability to rationally design compounds that will interact with ion channels and/or cell surface-localized receptors to have desired therapeutic effects, have been hampered by the lack of rapid, effective means to identify those compounds which interact with specific ion channels and/or specific cell surface-localized receptors.

The availability of rapid, effective means to identify compounds which interact with ion channels and/or cell surface-localized receptors would enable the rapid screening of a large number of compounds to identify those candidates suitable for further, in-depth studies of therapeutic applications.

The availability of rapid, effective means to determine if cells are producing functional ion channels and/or cell surface-localized receptors of a specific type would enable the rapid screening of cells for the presence of functional ion channels and/or surface-localized receptors that control passage across the cell membrane.

SUMMARY OF THE INVENTION

In accordance with the present invention, there are provided novel recombinant cells which are useful for assaying compounds for their agonist or antagonist activity with respect to specific ion channels and/or specific cell surface localized receptors. In addition, assay methods employing the invention recombinant cells are provided.

The invention assay methods provide rapid, reliable methods to identify compounds which interact with, and thereby affect the function of, specific ion channels and/or specific cell surface-localized receptors; as well as rapid reliable methods to determine if cells are producing specific functional ion channels and/or cell specific functional surface-localized receptors.

DETAILED DESCRIPTION OF THE INVENTION

In accordance with the present invention, there is provided a recombinant cell useful for assaying compounds to determine the agonist or antagonist activity of such compounds with respect to receptors of a specific type; wherein said receptors are present on the surface of said cell; and wherein said cell is transformed with a reporter gene construct comprising:

a transcriptional control element which is responsive to an intracellular condition that occurs when said receptor interacts with a compound having agonist or antagonist activity with respect to said receptor, and a reporter gene encoding a transcriptional and/or translational product; wherein said product can, directly or indirectly, be readily measured; and wherein said gene is in operative association with said transcriptional control element.

In accordance with another embodiment of the present invention, there is provided a method to assay compounds to determine the cell receptor agonist or antagonist activity thereof, said method comprising:

determining the level of the transcriptional and/or translational products of the reporter gene which is produced when a recombinant cell useful for assaying compounds (as described above; sometimes referred to herein as "receptor assay cell") is challenged with media containing the test compound, relative to the level of the transcriptional and/or translational products of the reporter gene which is produced when a negative control cell is challenged with media containing the test compound; wherein the negative control cell is identical to the receptor assay cell described above, except the negative control cell does not express the specific receptor type which is present on the surface of the receptor assay cell.

In accordance with yet another embodiment of the present invention, there is provided an alternate method to assay compounds to determine the cell receptor agonist or antagonist activity thereof, said method comprising:

determining the level of the transcriptional and/or translational products of the reporter gene which is produced when a receptor assay cell (as described above) is challenged with media containing the test compound, relative to the level of the transcriptional and/or translational products of the reporter gene which is produced when said receptor assay cell is challenged with control media not containing the test compound.

In accordance with still another embodiment of the present invention, there is provided a recombinant cell useful for assaying compounds to determine the agonist or antagonist activity of said compounds with respect to ion channels of a specific type; wherein said ion channels are present on the surface of said cell; and wherein said cell is transformed with a reporter gene construct comprising:

a transcriptional control element which is responsive to an intracellular condition that occurs when said ion channel interacts with a compound having agonist or antagonist activity with respect to said ion channel, and a reporter gene encoding a transcriptional and/or translational product; wherein said product can, directly or indirectly, be readily measured; and wherein said gene is in operative association with said transcriptional control element.

In accordance with a further embodiment of the present invention, there is provided a method to assay compounds to determine the ion channel agonist or antagonist activity thereof, said method comprising:

determining the level of the transcriptional and/or translational products of said reporter gene which is produced when a recombinant cell (as described above; sometimes referred to herein as "ion channel assay cell") is challenged with media containing the test compound, relative to the level of the transcriptional and/or translational products of the reporter gene which is produced when a negative control cell is challenged with media containing the test compound; wherein said negative control cell is identical to said ion channel assay cell (as described above) except said negative control cell does not express the specific ion channel which is present on the surface of the ion channel assay cell.

In accordance with a still further embodiment of the present invention, there is provided an alternate method to assay compounds to determine the ion channel agonist or antagonist activity thereof, said method comprising:

determining the level of the transcriptional and/or translational products of said reporter gene which is produced when an ion channel assay cell (as described above) is challenged with media containing the test compound, relative to the level of the transcriptional and/or translational products of the reporter gene which is produced when said cell is challenged with media which does not contain said test compound.

In accordance with the present invention, the level of reporter gene product expressed as a result of exposing a receptor or ion channel assay cell to a test compound is measured and compared to the level of reporter gene product expressed by a negative control cell, or compared to the level induced (in a cell of the invention) by a control (rather than test) compound. The intracellular signal to be transduced and, ultimately, measured, is generally initiated by a ligand interacting with a specific receptor or specific ion channel present on the cell surface. This interaction sets in motion a cascade of intracellular events, the ultimate consequence of which is a measurable change in transcription and/or translation of the reporter gene. An assay that provides a rapid indication of whether a specific receptor or ion channel, expressed on the surface of an eukaryotic cell, interacts with a test compound in a way that influences (either in a positive or negative manner) transduction of the intracellular cascade of events, and thus expression of the reporter gene, would provide a valuable screening tool for the development of compounds that act as agonists or antagonists of a cell receptor or ion channel.

The assays of this invention measure the end stage of the above described cascade of events, i.e., gene expression. This is accomplished through the use of a reporter gene expression construct which comprises a transcriptional control element and a reporter gene. The transcriptional control element is responsive to an intracellular condition that occurs when the cell receptor or ion channel of a specific type interacts with a compound having agonist or antagonist properties with respect to said receptor or ion channel. The reporter gene is placed in operational association with the transcriptional control element. The appearance of reporter gene product then serves as a readily observed indication of transcription, i.e., the reporter gene is selected from among those genes which encode a protein whose presence or absence is easily measurable.

The reporter gene expression construct is inserted into an eukaryotic cell which has present on its surface a receptor or ion channel of a specific type. The cell is then contacted with a test compound that may interact with the receptor or ion channel to initiate the intracellular cascade. If such interaction and cascade initiation occurs, the transcriptional control element responds to the specific intracellular alteration, resulting in an increase or decrease in transcription of the reporter gene. The reporter gene product is then assayed, the result of which is an indirect indication of the functional nature of the receptor- or ion channel-ligand interaction.

The assay of this invention is useful for determining functional ligand-receptor or ligand-ion channel interactions for at least three categories of cell surface-localized receptors which are presently known, i.e., ligand-gated ion channels and voltage-gated ion channels, and G protein-coupled receptors. Examples of each group include:

ligand-gated ion channels: nicotinic acetylcholine receptors, GABA (gamma-aminobutyric acid) receptors, excitatory receptors (e.g., glutamate and aspartate), and the like;

voltage-gated ion channels: calcium channels, potassium channels, sodium channels and the like;

G protein-coupled receptors: adrenergic receptors, muscarinic receptors and the like.

The invention assay is also useful for determining functional ligand-receptor interactions in cells containing a NMDA (N-methyl-D-aspartate) receptor, which has recently been categorized as being a ligand-gated, voltage-dependent ion channel.

Interaction of ligand with different members of each category of receptors and ion channels initiates a characteristic cascade of intracellular responses for members of that category. However, the specific responses exhibited by each group member are unique to that member. For instance, in the G-protein coupled receptor category, interactions of a ligand with a muscarinic acetylcholine receptor subtype initiates a cascade of events that begins with G-protein activation and ends with an alteration of cAMP level that influences gene expression. However, the specific influence on gene expression is unique to the specific G-protein-linked receptor in question, i.e., activation of human M1 receptors results in hydrolysis of phosphoinositols, whereas activation of human M3 receptors results in inhibition of adenylate cyclase. If a human M1 receptor-expressing cell also contains a reporter gene expression construct of this invention, then an appropriate transcriptional control element would be one which is capable of responding to the hydrolysis of phosphoinositols; and the reporter gene, functionally associated therewith, will be transcribed upon hydrolysis of phosphoinositol. Assay of the cells for the reporter gene product (directly or indirectly), and a comparison of the result with that from a negative control cell, or a control assay, provides a rapid indication as to the functional nature of the interaction of the human M1 receptor expressed on the cell with a test compound.

Likewise, functional interaction of a test compound with a voltage-gated calcium channel on a cell can be deduced by measuring the change in the level of reporter gene product which results when the intracellular calcium concentration is altered as a consequence of contacting the ion channel with a test compound that is an agonist or antagonist for this ion channel.

An example of a suitable transcriptional control element is the c-fos promoter which has elements therein which respond to, for example, calcium, cAMP (cyclic adenosine monophosphate), and NGF (nerve growth factor). An example of a reporter gene is CAT (chloramphenicol acetyl transferase), luciferase, and other enzyme detection systems, such as alkaline phosphatase, beta-galactosidase, and the like.

Other examples of transcriptional control elements contemplated for use in the practice of the present invention include the vasoactive intestinal peptide gene promoter (cAMP responsive), the somatostatin gene promoter (cAMP responsive), the proenkephalin promoter (responsive to cAMP, nicotinic agonists, and phorbol esters), the phosphoenolpyruvate carboxykinase gene promoter (cAMP responsive), the NGFI-A gene promoter (responsive to NGF, cAMP, and serum), and the like.

The development of cells which express a receptor or ion channel and a reporter gene expression construct, and which are useful for assay of compounds to determine their agonist or antagonist activity, is exemplified in the Examples provided herewith by reference to mammalian Ltk$^-$ cell lines which express the Type 1 human muscarinic (HM1) receptor and are transformed with a c-fos-CAT reporter gene expression construct. Those of skill in the art recognize that any cell line capable of transfection, and having low to no background level of the specific receptor or ion channel to be used in the invention assay is acceptable.

Similar receptor- or ion channel-expressing cell lines can be developed using, for example, the following receptor- or ion channel-encoding DNAs, transcriptional control elements, and reporter genes.

Exemplary receptors, in addition to those described above, include muscarinic receptors (e.g., human M2 (GenBank accession #M16404); rat M3 (GenBank accession #M16407); human M4 (GenBank accession M16405); human M5 (Bonner et al. (1988) *Neuron* 1:403–410); and the like); neuronal nicotinic acetylcholine receptors (e.g., the $\alpha_2$, $\alpha_3$ and $\beta_2$ subtypes disclosed in U.S. Ser. No. 504,455 (filed Apr. 3, 1990), hereby expressly incorporated by reference herein in its entirety); the rat $\alpha_2$ subunit (Wada et al. (1988) *Science* 240:330–334); the rat $\alpha_3$ subunit (Boulter et al. (1986) *Nature* 319:368–374); the rat $\alpha_4$ subunit (Goldman et al. (1987) *Cell* 48:965–973); the rat $\alpha_5$ subunit (Boulter et al. (1990) *J. Biol. Chem.* 265:4472–4482); the rat $\beta_2$ subunit (Deneris et al. (1988) *Neuron* 1:45–54); the rat $\beta_3$ subunit (Deneris et al. (1989) *J. Biol. Chem.* 264: 6268–6272); the rat $\beta_4$ subunit (Duvoisin et al. (1989) *Neuron* 3:487–496); and the like); GABA receptors (e.g., the bovine $\alpha_1$ and $\beta_1$ subunits (Schofield et al. (1987) *Nature* 328:221–227); the bovine $\alpha_2$ and $\alpha_3$ subunits (Levitan et al. (1988) *Nature* 335:76–79); the $\gamma$-subunit (Pritchett et al. (1989) *Nature* 338:582–585); the $\beta_2$ and $\beta_3$ subunits (Ymer et al. (1989) *EMBO J.* 8:1665–1670); the $\delta$ subunit (Shivers, B. D. (1989) *Neuron* 3:327–337); and the like); glutamate receptors (e.g., receptor isolated from rat brain (Hollmann et al. (1989) *Nature* 342:643–648); and the like); adrenergic receptors (e.g., human $\beta_1$ (Frielle et al. (1987) *PNAS* 84:7920–7924); human $\alpha_2$ (Kobilka et al. (1987) *Science* 238:650–656); hamster $\beta_2$ (Dixon et al. (1986) *Nature* 321:75–79); and the like; dopamine receptors (e.g., human D2 (Stormann et al. (1990) *Molec. Pharm.* 37:1–6); rat (Bunzow et al. (1988) *Nature* 336:783–787); and the like); NGF receptors (e.g., human NGF receptors (Johnson et al. (1986) *Cell* 47:545–554); and the like); serotonin receptors (e.g., human 5HT1a (Kobilka et al. (1987) *Nature* 329:75–79); rat 5HT2 (Julius et al. (1990) *PNAS* 87:928–932); rat 5HT1c (Julius et al. (1988) *Science* 241:558–564); and the like).

Exemplary ion channels, in addition to those described above, include calcium ion channels (e.g., human neuronal $\alpha_2$ subunit (see WO89/09834); rabbit skeletal muscle $\alpha 1$ subunit (Tanabe et al. (1987) *Nature* 328:313–318); rabbit skeletal muscle $\alpha 2$ subunit (Ellis et al. (1988) *Science* 241:1661–1664); rabbit skeletal muscle $\beta$ subunit (Ruth et al. (1989) *Science* 245:1115–1118); rabbit skeletal muscle $\gamma$ subunit (Jay et al. (1990) *Science* 248:490–492); and the like); potassium ion channels (e.g., rat brain (BK2) (McKinnon, D. (1989) *J. Biol. Chem.* 264:8230–8236); mouse brain (BK1) (Tempel et al. (1988) *Nature* 332:837–839); and the like); sodium ion channels (e.g., rat brain I and II (Noda et al. (1986) *Nature* 320:188–192); rat brain III (Kayano et al. (1988) *FEBS Lett.* 228:187–194); and the like).

Exemplary transcriptional control elements, in addition to those described above, include VIP gene promoter (cAMP responsive; Fink et al. (1988), *Proc. Natl. Acad. Sci.* 85:6662–6666); the somatostatin gene promoter (cAMP responsive; Montminy et al. (1986), *Proc. Natl. Acad. Sci.* 83:6682–6686); the proenkephalin promoter (responsive to cAMP, nicotinic agonists, and phorbol esters; Comb et al. (1986), *Nature* 323:353–356); the phosphoenolpyruvate carboxykinase gene promoter (cAMP responsive; Short et al. (1986), *J. Biol. Chem.* 261:9721–9726); the NGFI-A gene promoter (responsive to NGF, cAMP, and serum; Changelian et al. (1989). *Proc. Natl. Acad. Sci.* 86:377–381); and the like.

Exemplary reporter genes, in addition to those described above, include CAT (Alton and Vapnek (1979), *Nature* 282: 864–869); firefly luciferase (deWet et al. (1987), *Mol. Cell. Biol.* 7: 725–737); bacterial luciferase (Engebrecht and Silverman (1984), *PNAS* 1: 4154–4158; Baldwin et al. (1984), *Biochemistry* 23: 3663–3667); alkaline phosphatase (Toh et al. (1989), *Eur. J. Biochem.* 182: 231–238); and the like.

The invention will now be described in greater detail by reference to the following non-limiting examples.

EXAMPLES

Example I. DEVELOPMENT OF HM1-EXPRESSING, c-fos-CAT-CONTAINING MAMMALIAN CELLS Stable cell lines were developed to provide a transcription-based assay system by cotransfecting Ltk cells (mouse fibroblast thymidine kinase deficient) with a plasmid comprised of the HM1-encoding sequence, a selection plasmid comprised of either the wild-type or crippled TK gene, and a reporter gene expression construct.

A. Host Cells

HEK 293 available from ATCC (accession #CRL 1573)

LKt cells are available from ATCC (accession #CCL1.3).

COS7 available from ATCC (accession #CRL 1651)

DG44 (see L. Chasin (1986) *Cell. Molec. Genet.* 12: 555)

B. HM1 expression plasmid

The sequence of the HM1-encoding DNA fragment is described in Allard et al. (1987), *Nucl. Acids Res.* 15:10604. It can be obtained as described by Allard et al., or it can be isolated by screening a partial human genomic DNA library, comprised of 2.5–4.5 kb-sized EcoRI fragments in the λgtll vector, with an oligonucleotide homologous to nucleotides 250–279 of the HM1 sequence. Nucleotides 250–279 have the following sequence: ACG TAC CTG CTC ATG GGC CAC TGG GCT CTG. Screening conditions employed were as follows:

hybridization: 20% deionized formamide, 5 X Denhardt's, 6 X SSPE, 0.2% SDS, 200 µg/ml sonicated herring sperm DNA, 42° C.

wash: 0.2 X SSPE, 0.2% SDS, 50° C.

A positive clone was identified and confirmed to encode the HM1 receptor by DNA sequencing. The EcoRI insert of that clone was isolated and inserted into the EcoRI site of pIBI24 (International Biotechnologies, Inc., New Haven, Conn.), yielding clone pIBI24/HM1.

The HM1-encoding fragment of pIBI24/HM1 was modified for insertion into the SV40 promoter-based plasmid pSV2dhfr (see Subramani et al. (1981) *Mol. Cell. Biol.* 1: 854–864). Fifty nanograms of the 1.97 kb BamHI fragment from pIBI24/HM1 were ligated with 50 ng of BamHI-digested M13mp18. The ligation was transformed into *E. coli* strain JM103, and Amp$^R$ colonies were selected. Correct plasmid was identified by the presence of a 1.45 KpnI digestion fragment. Template was prepared from this plasmid to introduce an EcoRI site immediately before the initiation codon of the human HM1 coding region. This was accomplished by standard mutagenesis using an oligonucleotide of the following sequence: 5' CCC CAG CCC CAC CTT GAA TTC ATG AAC ACT TCA GCC 3' The mutagenesis products were transformed into JM103 and screened on plaque lifts with an oligonucleotide of the following sequence: 5' CAC CTT GAA TTC ATG AAC 3' Four of the positive clones were subjected to dideoxy sequencing and all were found to have the correct sequence. One of these, mHM1AChR103, was subjected to further mutagenesis to introduce an EcoRI site immediately following the human HM1 terminating codon. The mutagenizing oligonucleotide was of the following sequence: 5' CTC CCG CCA ATG CTG AGA ATT CTA TCT CCT GCA TCC C 3' Mutagenesis products were transformed into JM103 and screened on plaque lifts with an oligonucleotide of the following sequence: 5' CTG AGA ATT CTA TCT CC 3' Four of the positive clones were sequenced, and all had the correct sequence. One of these, M3HM1AR04, was digested with EcoRI and the 1.4 kb fragment representing the human M1 coding region was gel purified and eluted using DE-81 paper. Sixty nanograms of the 1.4 kb fragment were ligated with 20 ng of EcoRI-digested pUC19. Correct clones were identified by the presence of a 1.2 kb KpnI fragment. One of these was chosen and designated pHM1RO2. The 1.4 kb fragment was removed from pHM1RO2 and inserted (38.5 ng) into 50 ng of EcoRI-digested pSV2dhfr. The ligation was transformed into DH5α (Sombrook et al., *Molecular Cloning*, 2nd ed., CSH Lab, 1989, p. 10) cells and AmpR colonies were selected. Correct plasmid demonstrated bands of 1.4 and 5.0 kb upon digestion with EcoRI and 250, 1150, and 5000 bp bands upon digestion with PvuII. The final HM1 expression vector was called HM1pSV2dHFR.

C. TK+ Selection Plasmids

The TK+ plasmid cotransfected into Ltk$^-$ cells along with the muscarinic receptor-expressing plasmids was either pThx59 [Zipser, et al. (1981), *Proc. Natl. Acad. Sci.* 78:6276–6280] which encodes the wildtype TK gene, or pThx24 (ibid.) which encodes a crippled TK gene.

The starting material for construction of the TK+ selection plasmids was a hybrid plasmid containing the 3500 base pair BamHI DNA fragment of HSV-1 that encodes TK inserted into pBR322. The hybrid plasmid contains the TK promoter adjacent to the unique HindIII site of pBR322. Monomers of hybrid plasmid were linearized by partial digestion with HaeIII, linears were purified on agarose gels and portions of 5' sequence removed before the cap site of the TK gene. The linears were religated. Plasmids that, upon transfection into mammalian cells, expressed low levels of thymidine kinase were among the religated plasmids.

D. Reporter Gene Expression Plasmid

A reporter gene expression plasmid comprised of the CAT gene regulated by the c-fos promoter, plasmid pFC4 [(Deschamps et al., *Science* 230:1174–1177 (1985)], also was cotransfected into the cells.

Briefly, a 1.4 Kb NaeI (FC2) fragment from the human c-fos gene upstream region (van Straaten et al. (1983) *Proc. Natl. Acad. Sci. USA* 80:3183), which contains the c-fos promoter and upstream sequence was inserted using HindIII linkers into the vector, pSV2CAT (Gorman et al. (1982) *Mol. Cell Biol.* 2:1044) in place of the AceI-HindIII fragment in pSV2CAT. A series of plasmids were generated using by deleting portions of the upstream sequence from FC2. Deletion of the SstII to SstII fragment in FC2 yielded FC4. After the deleted fragments that correspond to the residual flanking sequences and fos promoter were digested with Hind III and separated by gel electrophoresis, they were cloned into the SmaI-HindIII digested DNA in place of the original 1.3 Kb fragment in pFC2 to produce pFC4.

In the constructs described below, unless indicated otherwise, the c-fos promoter region is obtained as the 400 bp fragment from pFC4, which includes a 500 bp insert from the c-fos promoter. The 5'- 100 base pair portion is derived from a noncontiguous distal upstream region.

E. Transfection and TK+ Selection

The CaPO$_4$ transfection procedure was used in the development of stable HM1-expressing cell lines. The protocol followed was that of Wigler, et al. (1979), *Proc. Natl. Acad. Sci.* 76:1373–1376.

Briefly, Ltk$^-$ cells were grown in nonselective medium [D+10 (Dulbecco's modified Eagle's medium+10% calf serum), 100 U/ml penicillin, and 100 µg/ml streptomycin] in a 10 cm-sized dish, to 20% confluence. The three circular vector DNAs were co-precipitated with CaPO$_4$ and added to the cell monolayer. The vector concentrations were as follows:

| | |
|---|---|
| Thx24:HM1:pFC4 | 2 µg:2 µg:2 µg/ml |
| Thx59:HM1:pFC4 | 0.25 µg:2 µg:2 µg/ml |

The transfected cells were allowed to grow for two days in nonselective medium. After two days, the cells were passed and non-selective media was replaced with HAT medium (D+10+15 μg/ml hypoxanthine+1 μg/ml aminopterin+5 μg/ml thymidine), and the cells were left to grow for 10–15 days, during which time the cells were "fed" fresh selective (HAT) medium every 3–4 days. After 10–15 days, colonies or clones appeared which indicated acceptance and expression of at least the plasmid carrying the TK gene. Colonies were transferred into separate wells of a 24-well dish and grown in selective medium for seven days, at which time individual clones were passed into 6-well dishes and grown for another seven days in selective medium. To provide cells for freezing and subsequent molecular and functional receptor analyses, the individual clones in the 6-well dishes were passed to 100 ml dishes.

Example II. DEVELOPMENT OF CONTROL CELL LINES

Two series of control cell lines were developed according to the methods in Example I.

The first series was developed by cotransfecting Ltk− cells with HM1 and TK+ DNAs as described in Example 1. These cell lines, examples of which were named LM159-10 and LM124-3, served as positive controls to show that activation of the expressed HM1 receptor led to an increase in endogenous c-fos RNA. These cell lines also served as negative controls to show that CAT mRNA or enzyme activity was not detected in the absence of the pFC4 reporter construct.

The second series of control cell lines was developed by cotransfecting Ltk− cells with pFC4 and TK+ DNAs. These cell lines, examples of which were called LFC4-3, LFC4-5, LFC4-7, LFC4-8, and LFC4-10, served as positive controls to show CAT mRNA and enzyme activity in response to compounds which activate the c-fos promoter. These cell lines also served as negative controls to show that CAT mRNA and enzyme activity were not altered when these cells were contacted with HM1 agonists or antagonists (because they do not express the HM1 receptor).

An additional negative control cell line was untransfected Ltk− cells, whereas a positive control cell line was PC12 cells (ATCC CRL1721).

Example III. CHARACTERIZATION OF CELL LINES

The cell lines employed in the practice of the present invention were then characterized by one or more of the following methods.

A. Analysis of HM1-, c-fos, and/or CAT-encoding RNA

The cell lines first were analyzed for expression of HM1-encoding RNA. Total RNA was isolated from $1 \times 10^7$ cells and 10–15 μg of each RNA were separated on a 1% agarose-formaldehyde gel, followed by transfer onto nitrocellulose. The northern blot was separately probed with one or more of the following probes:

HM1—random-primed 1.2 Kb EcoRI fragment from plasmid pSV2HM1

CAT—random-primed 788 bp TaqI fragment from plasmid pCaMVCN c-fos—random-primed 1.1 Kb PstI fragment from plasmid pvfos The hybridization and wash conditions were as follows: hybridization in 0.2X SSPE at room temperature wash at 65° C.

The expected sizes of the hybridizing bands are as follows:
HM1- ~3 kb
CAT - ~2 kb
c-fos −2.2 kb B. M1 receptor binding assay PC12 cells [Michel et al., Br. J. Pharmacol. 97:914–920 (1989)], and SH-SY5Y cells [Lambert et al., Eur. J. Pharmacol. 165:71–77 (1989); Serra et al., J. Neurochem. 50:1513–1521 (1988)] serve as a positive control for agonist and antagonist binding to HM1-expressing cells. Approximately $1 \times 10^6$ cells (control or invented) were incubated with 1.4 nM of the antagonist [$^3$H]-N-methyl-scopolamine (NMS) for 1 hr at 37° C., in the absence or presence of various concentrations of agonists, i.e., atropine, pirenzepine, carbamylcholine, scopolamine. Unbound labeled ligand was separated from cell-bound label by filtration of the assay mixture through Whatman GF/C filters, which had been pretreated with polyethyleneimine. The filters were washed with 4 ml of ice-cold assay buffer (144 mM NaCl, 4.7 mM KCl, 1.7 mM $KH_2PO_4$, 2.5 mM $CaCl_2 \cdot 2H_2O$, 1.1 mM $MgCl_2$, 10 mM glucose, 10 mM Tris/HCl), dried and analyzed in a scintillation counter to determine the amount of bound $^3$H-NMS. Counts bound in the presence of atropine were subtracted from counts bound in the absence of atropine to determine extent of specific binding.

The results of these competitive binding experiments yielded $IC_{50}$ values for displacement of specifically bound $^3$H-NMS as follows:

| Cell line | pirenzepine | carbamyl-choline | atropine | scopolamine |
| --- | --- | --- | --- | --- |
| PC12 | 900 nM | 200 μM | 7.0 nM | 5 nM |
| SH-SY5Y | 300 nM | 17 μM | 4.0 nM | 4 nM |
| LM159-10 | 200 nM | 1 mM | 4.5 nM | 2 nM |
| LM124-3 | 200 nM | >1 mM | 1.5 nM | 2 nM |
| LM1FC4-8 | 40 nM | 100 μM | 5.0 nM | 2 nM |
| LM1FC4-15 | 60 nM | 170 μM | 4.0 nM | 3 nM |

These results are in close agreement with those reported by Michael et al., Supra, for the muscarinic pharmacology of PC12 cells. Further, cell lines developed by transfection with HM1 or HM1 and c-fos-CAT expression vectors express HM1 receptors which exhibit expected pharmacological properties.

C. PI hydrolysis assay

The activation of the M1 muscarinic receptor by an agonist results in activation of the phosphotidyl inositol (PI) hydrolysis cascade. The functional assay involves labeling of cells with $^3$H-myo-inositol for 48 hrs. The cells then are treated with the muscarinic agonist, carbamylcholine (CCh), in the presence and absence of the muscarinic antagonist, atropine, for one hour before they are lysed and extracted in chloroform-methanol-water. Finally, the inositol phosphates are separated by ion exchange chromatography and quantitated by scintillation counting.

The protocol followed in this work is a modification of that reported in Sevva et al. (1986), Biochem. Biophys. Res. Comm. 140:160–166 and Peralta et al. (1988), Nature 334:434–437. Briefly, control cells (SHSY5Y or PC12 cells) and experimental cells were plated on 12-well plates (Costar) at a density of $5 \times 10^5$ cells/well and labeled with $^3$H-myo-inositol (3 μCi/well) for 65–70 hrs. The medium was decanted and the wells washed with 1 ml of 2X PI assay buffer (10 mM Hepes, 0.5 mM CaCl$_2$, 1 mM MgCl$_2$, 10 mM LiCl in 500 ml DMEM). The cells were then incubated with or without various concentrations of agonists, or incubated with agonist with or without various concentrations of antagonists, for 60 min at 37° C. The cells were then lysed and the suspension extracted with 3 ml of CHCl$_3$/MeOH (1:1). After centrifugation (3200 rpm for 5 min), the upper aqueous phase was removed and diluted with 2 ml H$_2$O and centrifuged again. The supernatants were then loaded on 1 ml Dowex 1X8 AG resin previously equilibrated with 5 mM myo-inositol. The columns were then washed with 9 ml of 5 mM myo-inositol followed by 8 ml of 60 mM sodium formate, 5 mM sodium borate. All of the inositol phosphates (IP1, IP2, IP3) were eluted together with 6 ml of 0.1M formic acid, 1M ammonium formate. 3 ml of the eluates were removed and counted with 20 ml scintillation fluid for analysis. Fold stimulation was determined by the cps agonist/cpm buffer control. EC$_{50}$ and IC$_{50}$ were determined by subtracting the buffer controls and plotting the agonist or antagonist with the percent maximum response (agonist only).

As in the receptor binding assays, SH-SY5Y (Serra et al., Supra) and PC12 [Horowitz, J., *J. Neurochem.* 53:197-204 (1989)] cells serve as positive control systems for activation of the PI hydrolysis pathway by muscarinic agonists and inhibition of the stimulation by muscarinic antagonists. In the positive control cell line SH-SY5Y, treatment with 1 mM CCh resulted in approximately 50-fold stimulation of inositol phosphate accumulation, which was blocked by 100 nM atropine. In the PC12 cells, treatment with 1 mM CCh resulted in 27-fold activation. The negative control cell line, 59-0 cells, did not respond to CCh treatment while the cells transfected with the M1 cDNA displayed varying levels of CCh stimulation. The stimulation observed with 1 mM CCh is summarized below for the positive control and transfected cell lines.

| Cell line | -Fold Stimulation | ED$_{50}$, μM |
|---|---|---|
| PC12 | 27 | 7 |
| SH-SY5Y | 48 | 18 |
| LM1/10 | 9 | 90 |
| LM1/24-3 | 28 | 48 |
| LM1/FC4-8 | 30 | 61 |
| LM1/FC4-15 | 4 | 48 |

The pharmacological properties of the transfected cell lines, LM1/24-3, LM1/10, LM1/FC4-8, and LM1/FC4-15 cells, as well the SH-SY5Y and PC12 cells were characterized by studying the dose-dependent inhibition of CCh-stimulated inositol phosphate accumulation by the muscarinic antagonists atropine, pirenzepine, and scopolamine. The IC$_{50}$ values obtained for the antagonists are tabulated in below:

| Cell line | Pirenzepine | Atropine | Scopolamine |
|---|---|---|---|
| PC12 | 900 μM | >100 nM | ND |
| SHSY5Y | 3.3 μM | 47 nM | 36 nM |
| LM159-10 | 0.5 μM | 13 nM | 31 nM |
| LM124-3 | 0.2 μM | 15 nM | 15 nM |
| LM1FC4-8 | 0.3 μM | 21 nM | 18 nM |
| LM1FC4-15 | ND | 10 nM | ND |

ND = not determined

D. Transcription-based assay

Control and invention cells to be employed in the invention transcription-based assay were treated as follows: cells were grown to 70-80% confluence and then grown in 0.5% serum media for two days prior to assay. This serum starvation step decreases background levels of c-fos promoter transcription. For each cell type to be assayed, groups of three plates of cells were similarly treated. The various treatments included treatment with 100-500 μM carbachol for 15-45 min, treatment with 20% serum for 15-45 min, no treatment, but were swirled as were the others, and treatment with 10 μM atropine for 5 min prior to treatment with carbachol. One plate in each group was incubated for 30-60 min at 37° C., and then used to isolate total RNA for northern analysis (see Example III.A.). The other two plates were incubated for 5 hr at 37° C. and then subjected to assay for CAT activity.

1. CAT assay

The CAT activity assay was conducted as follows: Protein lysates were prepared by washing the plates with phosphate-buffered saline (PBS) and then lysing cells on the plate in 500 μl 10.25M Tris.HCl pH7.8, 1% Triton X100. The lysate is transferred to an eppendorf tube and then incubated at 65° C. for 10 min. A 5 min spin in a microfuge at 4° C. was followed by transfer of the lysate to fresh tubes and freezing at −20° C. until time to assay.

At time of assay, BioRad protein assays were done in duplicate. 150 μl of cell lysate was used in the CAT assay. 90 μl of dH$_2$O, 0.5 μl 500 mM chloramphenicol, and 10 μl $^{14}$C-acetyl CoA or $^{3}$H-acetyl CoA were added to initiate the reaction, which was incubated for 1-4 hr at 37° C. The reaction was stopped on ice, and 300 μl cold ethyl acetate was added. The tubes were vortexed, spun in a microfuge for 1 min, and 200 μl of the organic phase was transferred to a glass scintillation vial. The 300 μl ethyl acetate extraction was repeated and the organic extracts were combined with 5 ml Econofluor scintillation counting solution. Radioactivity was determined in a scintillation counter.

2. Northern analysis

The RNA was probed for the presence of c-fos and CAT RNA as described in Example III.A.

3. Data analysis

Cell lines which had been transfected with plasmids containing the HM1 gene, e-g., LM159-10 and LM124-3, were analyzed for expression of endogenous c-fos RNA after treatment with the cholinergic agonist carbachol or carbachol and atropine, a muscarinic antagonist. If functional HM1 receptors are present on the surface of the cells, the carbachol should interact with the receptor, resulting in alteration of an intracellular condition to which the endogenous c-fos transcriptional control element is sensitive. The altered intracellular condition should activate the c-fos promoter and the c-fos gene should be transcribed at a higher level. The cascade should be detectable at the RNA level, by an induction of endogenous c-fos RNA. Furthermore, the M1 agonist-mediated induction of c-fos, should be blocked by M1 antagonists. All these results were achieved in cell lines LM159-10 and LM124-3, indicating that they do express HM1 receptors which are associated with a functional c-fos induction pathway.

| cell line atropine | no treatment | 100 μM carbachol | 100 μM carbachol + 10 μM |
| --- | --- | --- | --- |
| LM159-10 | − | +++ | + |
| LM124-3 | − | +++ | + |
| LtK⁻ | − | − | − |

In cells transfected with the HM1 expression vector plus the c-fos-CAT marker plasmid, e.g., LM1FC4-8 and LM1FC4-15, cells expressing functional HM1 receptors will likewise show an increase in c-fos mRNA upon interaction with an HM1 agonist. However, these cells should also demonstrate an increase in CAT-specific RNA and enzyme activity by nature of activation of the c-fos-CAT expression construct. All these results were achieved in cell line LM1FC4-15 upon treatment with an HM1 agonist (carbachol) and a general c-fos inducer (20% serum).

| Cell line | no treatment | 100 μM carbachol | 20% serum |
| --- | --- | --- | --- |
| LM1FC4-8 | | | |
| c-fos RNA | − | − | + |
| CAT RNA | + | + | + |
| CAT activity | + | + | + |
| LM1FC4-15 | | | |
| c-fos RNA | − | ++ | ++ |
| CAT RNA | + | ++ | ++ |
| CAT activity | + | ++ | ++ |
| LFC4-7 | | | |
| c-fos RNA | − | − | + |
| CAT RNA | + | + | ++ |
| CAT activity | + | + | ++ |

The invention has been described in detail with reference to certain particular embodiments thereof, but it will be understood that variations and modifications can be effected with the spirit and scope of the invention.

That which is claimed is:

1. A method for identifying compounds that modulate cell surface protein-mediated activity by detecting intracellular transduction of a signal generated upon interaction of the compound with the cell surface protein, comprising:

comparing the amount of transcription of a reporter gene or the amount of reporter gene product expressed in a first recombinant cell in the presence of the compound with the amount of transcription or product in the absence of the compound, or with the amount of transcription or product in a second recombinant cell; and selecting compounds that change the amount of transcription of a reporter gene or the amount of reporter gene product expressed in the first recombinant cell in the presence of the compound compared to the amount of transcription or product in the absence of the compound, or compared to the amount of transcription or product in the second recombinant cell, wherein:

the cell surface protein is a surface receptor or ion channel;

the first recombinant cell contains a reporter gene construct and expresses the cell surface protein;

the second recombinant cell is identical to the first recombinant cell, except that it does not express the cell surface protein; and the reporter gene constructs contains:

(a) a transcriptional control element that is responsive to the intracellular signal that is generated by the interaction of an agonist with the cell surface protein; and (b) a reporter gene that encodes a detectable transcriptional or translational product and that is in operative association with the transcriptional control element.

2. The method of claim 1, wherein said compound is an agonist or antagonist of said cell surface receptor or ion channel.

3. The method of claim 1, wherein the amount of transcription is determined by measuring the amount of mRNA that is transcribed from said reporter gene.

4. The method of claim 1, wherein the amount of transcription is measured by measuring the amount of reporter gene protein that is produced.

5. The method of claim 2, wherein said compound is an antagonist.

6. The method of claim 2, further comprising, prior to comparing the difference in the amount of transcription of the reporter gene, contacting the recombinant cell with an agonist that activates said cell surface protein, whereby transcription of said reporter gene is induced.

7. The method of claim 1, wherein said reporter gene construct includes a transcriptional regulatory region that includes a sequence of nucleotides that modulates transcription from said promoter in the absence of said cell surface protein or compound.

8. The method of claim 1, wherein the transcriptional control element includes a promoter selected from the group consisting of the c-fos gene promoter, the vasoactive intestinal peptide gene promoter, the somatostatin gene promoter, the proenkephalin gene promoter, the phosphoenolpyruvate carboxykinase gene promoter and the nerve growth factor-1 A gene promoter.

9. The method of claim 1, wherein the reporter gene is selected from the group consisting of the gene encoding bacterial chloramphenicol acetyltransferase, the gene encoding firefly luciferase, the gene encoding bacterial luciferase, and the gene encoding alkaline phosphatase.

10. The method of claim 1, wherein the transcriptional control region includes at least one regulatory element selected from the group consisting of serum responsive elements, cyclic adenosine monophosphate responsive elements, and elements responsive to intracellular calcium ion levels.

11. The method of claim 1, wherein the cell surface receptor is the Type 1 human muscarinic receptor, the promoter is the c-fos promoter and the reporter gene is the gene encoding bacterial chloramphenicol acetyltransferase.

12. The method of claim 1, wherein the cell surface receptor is selected from the group consisting of muscarinic receptors, neuronal nicotinic acetylcholine receptors, gamma aminobutyric acid receptors, glutamate receptors, adrenergic receptors, dopamine receptors, nerve growth factor receptors, and serotonin receptors.

13. The method of claim 1, wherein the ion channel is a calcium channel, potassium ion channel, or a sodium ion channel.

14. The method of claim 6, wherein said compound is an antagonist.

* * * * *

UNITED STATES PATENT AND TRADEMARK OFFICE
CERTIFICATE OF CORRECTION

Page 1 of 2

PATENT NO. : 5,401,629
DATED : March 28, 1995
INVENTOR(S) : HARPOLD, Michael M., and BRUST, Paul It is certified that error appears in the above-indentified patent and that said Letters Patent is hereby corrected as shown below:

ON THE TITLE PAGE:

Item [56]; OTHER PUBLICATIONS, Deschamps, et al., after "the" replace the misspelled "proto-oncogen" with -proto-oncogene-;
   at page 2, OTHER PUBLICATIONS, Kobilka, et al., after "the" replace the misspelled "fmaily" with -family-;
   at page 2, OTHER PUBLICATIONS, Tanabe, et al., after "channel" replace "b lockers" with the unspaced -blockers-;
   at page 2, OTHER PUBLICATIONS, Ellis, et al., after "of" replace "mRNAS" with -mRNAs-;
   at page 3, OTHER PUBLICATIONS, Alton and Vapnek, after "transposon" replace "tn9" with the capitalized -Tn9-;
   at page 3, OTHER PUBLICATIONS, Baldwin, et al., after "from" replace "vibrio" with the capitalized -Vibrio-; and
   at page 3, OTHER PUBLICATIONS, Baldwin, et al., after "in" replace "escherichia" with the capitalized -Escherichia-.

at column 6, line 57, Example I. DEVELOPMENT OF HM1-EXPRESSING, c-fos-CAT-CONTAINING MAMMALIAN CELLS, after "cotransfecting" replace "Ltk" with -Ltk$^-$-;
   at column 6, line 67, Example I. DEVELOPMENT OF HM1-EXPRESSING, c-fos-CAT-CONTAINING MAMMALIAN CELLS, at the beginning of the line, replace "LKt" with -Ltk$^-$-;

UNITED STATES PATENT AND TRADEMARK OFFICE
CERTIFICATE OF CORRECTION

PATENT NO. : 5,401,629
DATED : March 28, 1995
INVENTOR(S) : HARPOLD, Michael M.; and BRUST, Paul It is certified that error appears in the above-indentified patent and that said Letters Patent is hereby corrected as shown below:

at column 7, line 66, after "DH5a" replace the misspelled "(Sambrook" with -(Sambrook-;
at column 8, line 30, after "1.4" replace "Kb" with -kb-;
at column 8, line 44, after "1.3" replace "Kb" with -kb-;
at column 9, line 60, after "1.2" replace "Kb" with -kb-; and
at column 12, line 25, after "10.25M" replace "Tris.HCI" with -TrisHCI-.

Signed and Sealed this

Fourteenth Day of May, 1996

*Attest:*

BRUCE LEHMAN

*Attesting Officer*   Commissioner of Patents and Trademarks

US005401629C1

(12) EX PARTE REEXAMINATION CERTIFICATE (5879th)
United States Patent
Harpold et al.

(10) Number: US 5,401,629 C1
(45) Certificate Issued: Sep. 4, 2007

(54) ASSAY METHODS AND COMPOSITIONS USEFUL FOR MEASURING THE TRANSDUCTION OF AN INTRACELLULAR SIGNAL

(75) Inventors: Michael M. Harpold, San Diego, CA (US); Paul Brust, San Diego, CA (US)

(73) Assignee: Sibia Neurosciences, Inc., La Jolla, CA (US)

Reexamination Request:
No. 90/005,147, Oct. 9, 1998
No. 90/005,326, Apr. 12, 1999

Reexamination Certificate for:
Patent No.: 5,401,629
Issued: Mar. 28, 1995
Appl. No.: 07/563,751
Filed: Aug. 7, 1990

Certificate of Correction issued May 14, 1996.

(51) Int. Cl.
*G01N 33/566* (2006.01)
*G01N 33/567* (2006.01)

(52) U.S. Cl. .............................................. 435/6; 436/63
(58) Field of Classification Search ....................... None
See application file for complete search history.

(56) References Cited

U.S. PATENT DOCUMENTS

| | | | |
|---|---|---|---|
| 4,859,609 A | 8/1989 | Dull et al. | |
| 4,935,363 A | 6/1990 | Brown et al. | |
| 4,952,499 A | 8/1990 | Cantor et al. | |
| 4,980,281 A | 12/1990 | Housey et al. | |
| 4,985,352 A | 1/1991 | Julius et al. | |
| 5,026,635 A | 6/1991 | Ferguson et al. | |
| 5,063,154 A | 11/1991 | Fink et al. | |
| 5,071,773 A | 12/1991 | Evans et al. | 436/501 |
| 5,091,518 A | 2/1992 | Sucov et al. | |
| 5,144,007 A | 9/1992 | Pfahl | |
| 5,215,910 A | 6/1993 | Brown et al. | |
| 5,266,464 A | 11/1993 | Housey et al. | |
| 5,284,746 A | 2/1994 | Sledziewski et al. | 435/6 |
| 5,298,429 A | 3/1994 | Evans et al. | |
| 5,369,028 A | 11/1994 | Harpold et al. | 435/252.3 |
| 5,378,603 A | 1/1995 | Brown et al. | |
| 5,386,025 A | 1/1995 | Jay et al. | 536/23.5 |
| 5,407,820 A | 4/1995 | Ellis et al. | 435/240.2 |
| 5,426,177 A * | 6/1995 | Davis et al. | 530/395 |
| 5,462,856 A | 10/1995 | Lerner et al. | |
| 5,530,094 A | 6/1996 | Takakku et al. | |
| 5,576,210 A | 11/1996 | Sledziewski et al. | 435/254.21 |
| 5,580,722 A | 12/1996 | Foulkes et al. | |
| 5,618,678 A | 4/1997 | Kelly et al. | |
| 5,618,720 A | 4/1997 | Ellis et al. | 435/325 |
| 5,648,334 A * | 7/1997 | Davis et al. | 514/12 |
| 5,665,543 A | 9/1997 | Foulkes et al. | |
| 5,670,113 A | 9/1997 | Akong et al. | |
| 5,688,655 A | 11/1997 | Housey et al. | |
| 5,691,188 A | 11/1997 | Pausch et al. | |
| 5,698,435 A | 12/1997 | Robinson et al. | |
| 5,747,336 A | 5/1998 | Bonner et al. | 435/325 |
| 5,776,502 A | 7/1998 | Foulkes et al. | 424/617 |
| 5,789,196 A | 8/1998 | Heinenmann et al. | |
| 5,846,720 A | 12/1998 | Foulkes et al. | 435/6 |
| 5,849,897 A * | 12/1998 | Davis et al. | 536/23.5 |
| 5,863,733 A | 1/1999 | Foulkes et al. | 435/6 |

FOREIGN PATENT DOCUMENTS

| | | |
|---|---|---|
| JP | 62-272990 | 11/1987 |
| WO | WO 88/03168 | 10/1987 |
| WO | WO 89/09834 | 10/1989 |
| WO | WO 91/12273 | 8/1991 |

OTHER PUBLICATIONS

Changelian et al. Proc. Natl. Acad. Sci. USA, 86:377–381, 1989.*

Trueheart et al. Teo genes required for cell fusion during yeast conjugation. Molecular and Cellular Biology, Jul. 1987, vol. 7(7):2316–1328.*

Nomoto et al. Regulation of the yeast pheromone response pathway by G protein subunits. The EMBO J. 1990, vol. 9(3):691–696.*

George et al. Receptor density and cAMP accumulation in CHO cella exhibiting stable expression of a cDNA that encodes the beta2–adrenergic receptor. Biochem. Biophys. Comm. Jan. 29, 1988, vol. 150(2):665–672.*

Felder et al. A transfected m1 muscarinic acetylcholine receptor stimulates adenylate cyclase via phosphatidylinositol hydrolysis. J. Biol. Chem. Dec. 5, 1989.*

Alam, Jawed et al. *Reporter Genes: Application to the Study of Mammalian Gene Transcription*, Analytical Biochemistry 188, pp. 245–254 (1990).

McLean, Stafford *Receptors and Receptor Binding Methods in Drug Discovery*, Molecular and Cellular Mechanisms of Septic Shock, pp. 109–128 (1989).

Zoon, K.C. et al. *Cell Receptor Assays*, Journal of Pharmaceutical & Biomedical Analysis, vol. 7, No. 2, pp. 147–154 (1989).

Burch, Ronald M. et al. *Mass Receptor Screening for New Drugs*, Pharmaceutical Research, vol. 8, No. 2 pp. 141–147 (1991).

Strosberg, A. Donny et al. *Receptor–Based Assays*, Current Opinion in Biotechnology, vol. 2, pp. 30–36 (1991).

Schilling, Karl et al. *Regulation of a fos–lacZ fusion gene: A Paradigm for Quantitative Analysis of Stimulus–Transcription Coupling*, Proc. National Academy of Science, vol. 88, pp. 5665–5669 (1991).

Arenander et al., "Induction of c–fos and TIS genes in cultured rat astrocytes by neurotransmitters," *J. of Neuroscience Research*, 24:107–114, 1989.

Deschamps et al., "Identification of a transcriptional enhancer element upstream from the proto–oncogene fos," *Science*, 230:1174–1177, 1985.

(Continued)

*Primary Examiner*—John Ulm

(57) ABSTRACT

Recombinant cells are provided which are useful for assaying compounds for their agonist or antagonist activity with respect to ion channels and/or cell surface-localized receptors. In addition, assay methods employing the invention recombinant cells are provided.

OTHER PUBLICATIONS

Fisch et al., "An AP1–binding sits in the c–fos gene can mediate induction by epidermal growth factor and 12–o–tetradecanoyl phorbol–13–acetate," *Molecular and Cellular Biology,* 9(3):1327–1331, 1989.

Lamb et al., "Demonstration in living cells of an intragenic negative regulatory element within the rodent c–fos gene," *Cell,* 61(3):485–496, 1990.

Montminy et al., "Binding of a nucleur protein to the cyclic–AMP response element of the somatostatin gene," *Nature,* 328:175–178, 1987.

Montminy et al., "Identification of a cyclic–AMP–responsive element within the rat somatostatin gene," *Proc. Natl. Acad. Sci. U.S.A.,* 83(18):6682–6686, 1986.

Montminy et al, "Regulation of cAMP–inducibte genes by CREB," *Trends Neurosci,* 13(5):184–188, 1990.

Peralta et al., "Differential regulation of PI hydrolyers and adenylyl cyclase by muscarinic receptor subtypes," *Nature,* 334(4):434–437, 1988.

Riabowol et al., "The catalytic subunit of cAMP–dependent protein kinase induces expression of genes containing cAMP–responsive enhancer elements," *Nature,* 336:83–86, 1988.

Sheng et al., "Calcium and growth factor pathways of c–fos transcriptional activation require distinct upstream regulatory sequences," *Molecular and Cellular Biology,* 8(7):2787–2796, 1988.

Alton, et al., "Nucleotide sequence analysis of the chloramphenicol resistance transposon Tn9," Nature 282:864–869 (1979).

Baldwin, et al., "Cloning of the luciferase structural gene from *Vibrio harveyi* and expression of bioluminescence in *Escherichia coli,*" Biochemistry 20:3663–3667 (1984).

Bonner, et al., "Cloning and expression of the human and rat m5 muscarinic acetylcholine receptor genes," Neuron 1:403–410 (1988).

Boulter, et al., "Isolation of a cDNA clone coding for a possible neural nicotinic acetylcholine receptor $\alpha$–subunit," Nature 319:368–374 (1986).

Boulter, et al., "$\alpha 3$, $\alpha 5$, and $\beta 4$: Three members of the rat neuronal nicotinic acetylcholine receptor–related gene family form a gene cluster," JBC 265:268–272 (1990).

Bunzow, et al., "Cloning and expression of a rat $D_2$ dopamine receptor cDNA," Nature 336:783–787 (1988).

Changelian, et al., "Structure of the NGFI–A gene and detection of upstream sequences responsible for its transcriptional induction by nerve growth factor," PNAS 86:377–381 (1989).

Collins, et al., "cAMP stimulates transcription of the $\beta_2$–adrenergic receptor gene in response to short–term agonist exposure," PNAS 86:4853–4857 (1989).

Comb, et al., "A cyclic AMP– and phorbol ester–inducible DNA element," Nature 323:353–356 (1986).

Deneris, et al., "Primary structure and expression of $\beta 2$: A novel subunit of neuronal nicotinic acetylcholine receptors," Neuron 1:45–54 (1988).

Deneris, et al., "$\beta 3$: A new member of nicotinic acetylcholine receptor gene family is expressed in brain," JBC 264:6268–6272 (1989).

DeWet, et al., "Firefly luciferase gene: Structure and expression in mammalian cells," Mol. Cell. Biol. 7:725–737 (1987).

Dixon, et al., "Cloning of the gene and cDNA for mammalian b–adrenergic receptor and homology with rhodopsin," Nature 321:75–79 (1986).

Duvoisin, "the functional diversity of the neuronal nicotinic acetylcholine receptors is increased by a novel subunit: $\beta 4$," Neuron 3:487–496 (1989).

Ellis, et al., "Sequence and expression of mRNAs encoding the $\alpha 1$ and $\alpha 2$ subunits of a DHP–sensitive calcium channel," Science 241:1661–1664 (1988).

Engebrecht, et al., "Identification of genes and gene products necessary for bacterial bioluminescence," PNAS 32:4154–4158 (1984).

Fink, et al., The CGTCA sequence motif is essential for biological activity of the vasoactive intestinal peptide gene cAMP–regulated enhancer, PNAS 85:6662–6666 (1988).

Frielle, et al., "Cloning of the cDNA for the human $\beta 1$–adrenergic receptor," PNAS 84:7920–7924 (1987).

Goldman, et al., "Members of a nicotinic acetylcholine receptor gene family are expressed in different regions of the mammalian central nervous system," Cell 48:965–973 (1987).

Hollmann, et al., "Cloning by functional expression of a member of the glutamate receptor family," Nature 342:643–648 (1989).

Jay, et al., "Primary structure of the $\gamma$ subunit of the DHP–sensitive calcium channel from skeletal muscle," Science 248:490–492 (1990).

Johnson, et al., "expression and structure of the human NGF receptor," Cell 47:545–554 (1986).

Julius, et al., "Molecular characterization of a functional cDNA encoding the serotonin lc receptor," Science 241:558–564 (1988).

Julius, et al., "The 5HT2 receptor defines a family of structurally distinct but functionally conserved serotonin receptors," PNAS 87:928–932 (1990).

Kayano, et al., "Primary structure of rat brain sodium channel III deduced from the cDNA sequence," FEBS Letters 228:187–194 (1988).

Kobilka, et al., "an intronless gene encoding a potential member of the family of receptors coupled to guanine nucleotide regulatory proteins," Nature 329:75–79 (1987).

Kobilka, et al., "Cloning, sequencing, and expression of the gene coding for the human platelet $\alpha_2$–adrenergic receptor," Science 321:650–656 (1987).

Levitan, et al., "Structural and functional basis for GABA, receptor heterogeneity," Nature 335:76–79 (1988).

McKinnon, "Isolation of a cDNA clone coding for a putative second potassium channel indicates the existence of a gene family," JBC 264:8230–8236 (1989).

Noda, et al., "existence of distinct sodium channel messenger RNAs in rat brain," Nature 320:188–192 (1986).

Pritchett, et al., "Importance of a novel $GABA_A$, receptor subunit for benzodiazephine pharmacology," Nature 338:582–585 (1989).

Ruth, et al., "Primary structure of the $\beta$ subunit of the DHP–sensitive calcium channel from skeletal muscle," Science 245:1115–1118 (1989).

Schofield, et al., "Sequence and functional expression of the $GABA_A$, receptor shows a ligand–gated receptor super–family," Nature 328:221–227 (1987).

Sheng, et al., "the regulation and function of c–fos and other immediate early genes in the nervous system," Neuron, 4:477–485 (1990).

Shivers, et al., "two novel distinct $GABA_A$, receptor subunits exist in distinct neural subpopulations," Neuron 3:327–337 (1989).

Short, et al., "Characterization of the phosphoenolpyruvate carboxykinase (GTP) promoter–regulatory region," JBC 261:9721–9726 (1986).

Stormann, et al., "Molecular cloning and expression of a dopamine D2 receptor from human retina," Molec. Pharm. 37:1–6 (1989).

Tanabe, et al., "Primary structure of the receptor for calcium channel blockers from skeletal muscle," Nature 328:313–318 (1987).

Tempel, et al., "Cloning of a probable potassium channel gene from mouse brain," Nature 332:837–839 (1988).

Toh, et al., "Isolation and characterization of a rat liver alkaline phosphatase gene," Eur. J. Biochem. 182:231–237 (1989).

Visvader, et al., "Two adjacent promoter elements mediate nerve growth factor activation of the c–fos gene and bind distinct nuclear complexes," PNAS 85:9474–9478 (1988).

Wada, et al., "functional expression of a new pharmacological subtype of brain nicotinic acetylcholine receptor," Science 240:330–334 (1988).

Ymer, et al., "$GABA_A$ receptor β subunit heterogeneity: Functional expression of cloned cDNAs," EMBO J 8:1665–1670 (1989).

Balduzzi, et al., "Specific inhibition of tyrosine kinase activity by an antibody to the v–ros oncogene product," J. Virology 60:765–767 (1986).

Bayne, et al., "Expression, purification and characterization of recombinant insulin–like growth factor I in yeast," Gene 66:235–244 (1988).

Berkhoat, et al., "Transfection of genes encoding the T cell receptor–associated CD3 complex in COS cells results in assembly of the macromolecular structure," J. Biol. Chem. 263:8528–8536 (1988).

Bitter, et al., "Expression and secretion vectors for yeast," Meth. Enzym. 153:516–544 (1987).

Bonner, et al., "Identification of a family of muscarinic acetylcholine receptor genes," Science 237:527–532 (1987).

Bouvier, et al., "Expression of a human cDNA encoding the $β_2$–adrenergic receptor in Chinese hamster fibroblasts (CHW): Functionality and regulation of the expressed receptors," Mol. Pharm. 33:133–139 (1987).

Brann, et al., "Expression of a cloned muscarinic receptor in A9 L cells," Mol. Pharm. 32:450–455 (1987).

Buckley, et al., "Antagonist binding properties of five cloned muscarinic receptors expressed in CHO–K1 cells," Molec. Pharmacol. 35:469–476 (1989).

Chan, et al., "Isolation and genetic analysis of *Saccharomyces cerevisiae* mutants supersensitive to G1 arrest by a Factor and α Factor pheromones," Mol. Cell. Biol. 2:11–20 (1982).

Colton, et al., "Development of an assay for $H_2$–receptor antagonists using isolated fat cells," J. Pharm. Meth. 3:253–266 (1980).

Condorelli, et al., "Induction of protoconcogene fos by extracellular signals in primary glial cultures," J. Neurosci. Res. 23:234–239 (1989).

Conklin, et al., "Stimulation of arachidonic acid release and inhibition of mitogenesis by cloned genes for muscarinic receptor subtypes stably expressed in A( L cells," Proc. Nat'l Acad. Sci 85:8698–8702 (1988).

Damante, et al., "IGF–I increases c–fos expression in FRTL5 rat thyroid cells by activating the c–fos Promoter," Biochem. Biophys. Res. Comm 151:1194–1199 (1988).

Dunphy, et al., "Yeast and mammals utilize similar cytosolic components to drive protein transport through the Golgi complex," Proc. Nat'l Acad. Sci. USA 83:1622–1626 (1986).

Elliot, et al., "Secretion of glycosylated human erythropoietin from yeast directed by the α–factor leader region," Gene 79:167–180 (1989).

Emorine, et al., "Structure of the gene for human $β_2$–adrenergic receptor: Expression and promoter characterization," Proc. Nat'l Acad. Sci. USA 84:6995–6999 (1987).

Felder, et al., "A transfected m muscarinic acetylcholine receptor stimulates adenylate cyclase via phosphatidylinositol hydrolysis," J. Biol. Chem. 264:20356–20362 (1989).

Finn, et al., "Binding and autophosphorylating activity of human insulin analogs," Biol. Chem. Hoppe Seyler 370:559–564 (1989).

Fischer, et al., "Glycosylation of the human interferon–γ receptor," J. Biol. Chem. 265:1710–1717 (1990).

Fraser et al., "Cloning, sequence analysis, and permanent expression of a human alpha2–adrenergic receptor in Chinese hamster ovary cells. Evidence for independent pathways of receptor coupling to adenylate cyclase attenuation and activation," J Biol Chem 264:11754–11761 (1989).

George, et al., "Receptor density and cAMP accumulation analysis in CHO cells exhibiting stable expression of a cDNA that encodes the $beta_2$–adrenergic receptor," Biochem. Biophys. Res. Comm. 150:665–672 (1988).

Gubits, et al., "Adrenergic receptors mediate changes in c–fos mRNA levels in brain," Molec. Brain Res. 6:39–45 (1989).

Hadcock, et al., "Down–regulation of β–adrenergic receptors: Agonist–induced reduction in receptor mRNA levels," Proc. Nat'l Acad. Sci. USA 85:5021–5025 (1988).

Hempstead, et al., "Expression of functional nerve growth factor receptors after gene transfer," Science 243:373–375 (1989).

Janssens, "The evolution and origin of eukaryotic transmembrane signal transduction," Comp. Biochem. Physiol. 90:209–223 (1987).

Ji, et al., "N–linked oligosaccharides are not required for hormone binding of the lutropin receptor in a Leydig tumor cell line and rat granulosa cells," Endocrinology 127:494–496 (1990).

Johnston, et al., "Sequences that regulate the divergent GAL1–GAL10 promoter in *Saccharomyces cerevisiae*," Mol. Cell. Biol. 4:1440–1448 (1984).

Kang, et al., "Effects of expression of mammalian Gα and hybrid mammalian–yeast Gα proteins on the yeast pheromone response signal transduction pathway," Molec. Cell. Biol. 10:2582–2590 (1990).

Kingsman, et al., "The production of mammalian proteins in *Saccharomyces cerevisiae*," TIBTech 5:53–57 (1987).

Kline et al., "Fertilization events induced by neurotransmitters after injection of mRNA in *Xenopus* eggs," Science 241:464–467 (1988).

Kobilka, et al., "Functional activity and regulation of human b2–adrenergic receptors expressed in *Xenopus* oocytes," J Biol. Chem. 262:15796–802 (1987).

Kousvelari, et al., "Regulation of proto–oncogenes in rat paratoid acinar cells in vitro after stimulation of β–adrenergic receptors," Experimental Cell Research 179:194–203 (1988).

Lefkowitz, "The new biology of drug receptors," Biochem. Pharmacol. 38:2941–2948 (1987).

Lesueur, et al., "Prolactin stimulates milk protein promoter in CHO cells. contransfected with prolactin receptor DNA," Molec. Cell. Endocrinol. 71:R7–R12 (1990).

Levitsky, "From epinephrine to cyclic AMP," Science 241:800–806 (1988).

Matsui, et al., "Independent expression of human a or b platelet–derived growth factor receptor cDNAs in a naive hematopoietic cell leads to functional coupling with mitogenic and chemotactic signaling pathways," Proc. Nat'l Acad. Sci. USA 86:8314–8318 (1989).

Mei, et al., "Pharmacological characterization of the M1 muscarinic receptors expressed in murine fibroblast B82 cells," J. Pharmacol. Experimental Therapeut. 248:661–670 (1989).

Mellon, et al., "Regulation of transcription by cyclic AMP–dependent protein kinase," Proc. Nat'l Acad. Sci. USA 86:4887–4891 (1989).

Miyajima, et al., "Suppressors of a gpa1 mutation cause sterility in *Saccharomyces cerevisiae*," Genetics 119:797–804 (1988).

Neve, et al., "Functional characterization of a rat dopamine D–2 receptor cDNA expressed in a mammalian cell line," Molec. Pharmacol. 36:446–451 (1989).

Novick et al., "Identification of 23 complementation groups required for post–translational events in the yeast secretory pathway," Cell 21:205–215 (1980).

Orser, et al., "The *Escherichia coli proB* gene corrects the proline auxotrophy of *Saccharomyces cerevisiae pro1* mutants," Molec. Gen. Genet. 23:124–128 (1988).

Payette, et al., "Expression and pharmacological characterization of the human M1 muscarinic receptor in *Saccharomyces cerevisiae*," FEBS Letters 266:21–25 (1990).

Regan, et al., "Cloning and expression of a human cDNA for an $\alpha_2$–adrenergic receptor subtype," Proc. Nat'l Acad. Sci. USA 85:6301–6305 (1988).

Rosenfeld, et al., "Developmental and hormonal regulation of neuroendocrine gene transcription," Recent Prog. Hormonal Research 43:499–534 (1987).

Scheckman, "Protein localization and membrane traffic in yeast," Ann. Rev. Cell Biol. 1:115–143 (1985).

Sheng, et al., "Calcium and growth factor pathways of c–fos transcriptional activation require distinct upstream regulatory sequences," Mol. Cell. Biol. 8:1787–1796 (1988).

Schild, et al., "Cloning of three human multifunctional de novo purine biosynthetic genes by functional complementation of yeast mutations," Proc. Nat'l Acad. Sci. 87:2916–2920 (1990).

Siebenlist, et al., "Promoter region of interleukin–2 gene undergoes chromatin structure and confers inducibility of chloramphenicol acetyltransferase gene during activation of T cells," Mol. Cell. Biol. 6:3042–3049 (1986).

Siekevitz, et al., "Activation of the HIV–1 LTR by T cell mitogens and the trans–activator protein HTLV–I" Science 238:1575–1578 (1987).

Sikorski, et al., "A system of shuttle vectors and yeast host strains designed for efficient manipulation of DNA in *Saccharomyces cerevisiae*," Genetics 122:19–27 (1989).

Sistonen, et al., "Activation of the neu tyrosine kinase induces the fos/jun transcription factor complex, the glucose transporter and ornithine decarboxylase," J. Cell Biol. 109:1911–1919 (1989).

Snyder, "Drug and neurotransmitter receptors," JAMA 261:3126–3129 (1989).

Squinto, et al., "Platelet–activating factor stimulates a fos/jun/AP–1 transcriptional signaling system in human neuroblastoma cells," J. Neurosci. Res. 24:558–566 (1989).

Stein, et al., "Cloned M1 muscarinic receptors mediate both adenylate cyclase inhibition and phosphoinositide turnover," EMBO J. 7:3031–3035 (1988).

Tong–Starksen, et al., "Human immunodeficiency virus long terminal repeat responds to T–cell activation signals," Proc. Nat'l Acad. Sci. USA 84:6845–6849 (1987).

Trueheart, et al., "two genes required for cell fusion during yeast conjugation" Evidence for a pheromone–induced surface protein, Mol. Cell. Biol. 7:2316–2328 (1987).

Usui, et al., "Cyclic AMP–responsive region of the human proopiomelanocortin (POMC) gene," Molec. Cell. Endocrinol. 62:141–146 (1989).

Utsumi, et al., "Activation of bacterial porin gene expression by a chimeric signal transducer in response to aspartate," Science 245:1246–1249 (1989).

Changelian, P.S. et al., "Structure of the NGFI–A gene and detection of upstream sequences responsible for its transcriptional induction by nerve growth factor," *Pro. Natl. Acad. Sci. USA,* 86:377–381 (1989).

Blackshear et al. "Protein Kinase C–dependent and –independent Pathways of Proto–oncogene Induction in Human Astrocytoma Cells" *The Journal of Biological Chemistry* vol. 262, No. 16; 7774–7781 (1987).

Chen et al. "Requirement for Intrinsic Protein Tyrosine Kinase in the Immediate and Late Actions of the EGF Receptor" *Nature* 328:820–823 (1987).

Comb et al. "A Cyclic AMP– and Phorbol Ester–Inducible DNA Element" *Nature,* vol. 323, pp. 354–356 (1986).

Deutsh et al. "Cyclic AMP and Phorbol Ester–Stimulated Transcription Mediated by Similar DNA Elements That Bind Distinct Proteins" *Proc. Natl. Acad. Sci. USA,* vol. 85, pp. 7922–7926 (1988).

Peralta et al. "Distinct Primary Structures, Ligand–Binding Properties and Tissue–Specific Expression of Four Human Muscarinic Acetylcholine Receptors" *The EMBO Journal* vol. 6; 3923–3929 (1987).

Sassone–Corsi et al. "Induction of Proto–Oncogene fos Transcription Through the Adenylate Cyclase Pathway: Characterization of a cAMP–Responsive Element" *Genes & Development,* pp. 1529–1538 (1988).

Stumpo et al. "Identification of a c–fos, Sequences Involved in Induction by Insulin and Phorbol Esters" *Journal of Biological Chemistry* 263:1611–1614 (1988).

Lester, H.A. "Heterologous Expression of Excitability Proteins: Route to More Specific Drugs?" *Science 241*:1057–1063 (1988).

\* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1 to 52 are cancelled.

* * * * *